United States Patent
Youssef et al.

(10) Patent No.: US 11,684,497 B2
(45) Date of Patent: Jun. 27, 2023

(54) INTRALUMINAL VESSEL PROSTHESIS SYSTEM

(71) Applicant: JOTEC GmbH, Hechingen (DE)

(72) Inventors: Marwan Youssef, Mainz (DE); Christian Woerne, Ostfildern (DE); Michael Walther, Lentfoehrden (DE)

(73) Assignee: JOTEC GmbH, Hechingen (DE)

( * ) Notice: Subject to any disclaimer, the term of this patent is extended or adjusted under 35 U.S.C. 154(b) by 269 days.

(21) Appl. No.: 16/806,174

(22) Filed: Mar. 2, 2020

(65) Prior Publication Data

US 2020/0214857 A1 Jul. 9, 2020

Related U.S. Application Data

(63) Continuation of application No. PCT/EP2018/074019, filed on Sep. 6, 2018.

(30) Foreign Application Priority Data

Sep. 8, 2017 (DE) ...................... 10 2017 120 819.4

(51) Int. Cl.
*A61F 2/852* (2013.01)
*A61F 2/86* (2013.01)

(52) U.S. Cl.
CPC ............... *A61F 2/852* (2013.01); *A61F 2/86* (2013.01)

(58) Field of Classification Search
CPC ........ A61F 2250/0063; A61F 2002/061; A61F 2/856; A61F 2002/821; A61F 2002/828; A61F 2/852
See application file for complete search history.

(56) References Cited

U.S. PATENT DOCUMENTS 6,645,242 B1 11/2003 Quinn
2006/0195177 A1 8/2006 Kaufmann et al.
(Continued)

FOREIGN PATENT DOCUMENTS

CN 102740807 A 10/2012
CN 103517686 A 1/2014
(Continued)

OTHER PUBLICATIONS

First Office Action (Including Translation) for corresponding Chinese Patent Application No. 201880058167.7, dated Jun. 18, 2021.
(Continued)

*Primary Examiner* — Thomas McEvoy
(74) *Attorney, Agent, or Firm* — Jason H. Vick; Sheridan Ross, PC

(57) ABSTRACT

The present invention relates to an intraluminal vessel prosthesis system for implantation in the region of the aortic arch of a patient, comprising a hollow cylindrical main vessel prosthesis, wherein the hollow cylindrical main vessel prosthesis is configured and dimensioned for implantation in the region of the artic arch and the descending aorta (Aorta descendens) of the patient and wherein the main vessel prosthesis, at least over part of the length L2 of the anchoring vessel prosthesis, and wherein the diameter D2 of the anchoring vessel prosthesis is at least 45% smaller than the diameter D1 of the main vessel prosthesis and wherein the length L2 of the anchoring vessel prosthesis is shorter than the length L2 of the main vessel prosthesis.

19 Claims, 4 Drawing Sheets

(56) References Cited

U.S. PATENT DOCUMENTS

| | | | | |
|---|---|---|---|---|
| 2006/0247761 | A1* | 11/2006 | Greenberg | A61F 2/07 623/1.3 |
| 2010/0042201 | A1* | 2/2010 | Sherif | A61F 2/90 606/228 |
| 2011/0319983 | A1* | 12/2011 | Zhu | A61F 2/07 623/1.35 |
| 2013/0013050 | A1 | 1/2013 | Shalev et al. | |
| 2013/0079870 | A1 | 3/2013 | Roeder et al. | |
| 2014/0081317 | A1 | 3/2014 | Zanatta et al. | |
| 2014/0094902 | A1 | 4/2014 | Khoury | |
| 2014/0277348 | A1* | 9/2014 | Roeder | A61F 2/07 623/1.11 |
| 2015/0234957 | A1 | 8/2015 | Leotta et al. | |
| 2015/0250626 | A1 | 9/2015 | Fischer et al. | |
| 2017/0007392 | A1 | 1/2017 | Lourenco et al. | |
| 2018/0303598 | A1 | 10/2018 | Szopinski et al. | |

FOREIGN PATENT DOCUMENTS

| | | |
|---|---|---|
| CN | 103747761 A | 4/2014 |
| CN | 104066401 A | 9/2014 |
| CN | 104936552 A | 9/2015 |
| DE | 10065824 A1 | 7/2002 |
| DE | 10337739 A1 | 3/2005 |
| EP | 1245202 A1 | 10/2002 |
| EP | 1336393 A2 | 8/2003 |
| EP | 2740441 A1 | 6/2014 |
| EP | 2777610 A1 | 9/2014 |
| JP | 2013-071005 A | 4/2013 |
| JP | 2014-526929 A | 10/2014 |
| WO | WO 01/56500 | 8/2001 |
| WO | WO 2010/024879 | 3/2010 |
| WO | WO 2013/025727 | 2/2013 |
| WO | WO 2013/074990 | 5/2013 |
| WO | WO 2013/155306 A1 | 10/2013 |
| WO | WO 2017/114879 | 7/2017 |

OTHER PUBLICATIONS

International Search Report for International Application No. PCT/EP2018/074019, dated Dec. 7, 2018.
Written Opinion for International Application No. PCT/EP2018/074019, dated Dec. 7, 2018.
Office Action for German Patent Application 10 2017 120 819.4, dated May 11, 2018.
Notice of Reasons for Refusal (Including Translation) for Japanese Patent Application No. 2020-513856, dated Mar. 2, 2021.
International Preliminary Report on Patentability for International Application No. PCT/EP2018/074019, dated Mar. 19, 2020.

* cited by examiner

INTRALUMINAL VESSEL PROSTHESIS SYSTEM

CROSS REFERENCES TO RELATED APPLICATIONS

This application is a continuation of international patent application PCT/EP2018/074019, filed on Sep. 6, 2018, designating the U.S., which international patent application has been published in German language and claims priority from German patent application DE 10 2017 120 819.4, filed on Sep. 8, 2017. The entire contents of these priority applications are incorporated herein by reference.

BACKGROUND

The present invention relates to an intraluminal vascular prosthesis and to an intraluminal vascular prosthesis system for implantation in the region of the aortic arch of a patient.

Vascular implants of this kind are known in the prior art, for example from DE 103 37 739.5.

It is generally known for intraluminal vascular prostheses, also referred to as endovascular stents or stent grafts, to be implanted in order to treat weakened, damaged or torn vessels or aneurysms. For this purpose, a vascular prosthesis or a stent graft is released at the diseased or damaged site of the vessel and restores the functionality of the original vessel or supports the still existing integrity of the vessel.

An aneurysm is understood here as a widening or bulging of an arterial blood vessel as a consequence of congenital or acquired lesions of the wall. The bulge in this case can affect the vessel wall as a whole or, in what is called a false aneurysm or dissection, blood flows from the lumen of the vessel in between the layers of the vessel wall and tears these apart from one another. Non-treatment of an aneurysm may lead to a rupture of the artery in advanced stages, after which the patient suffers internal bleeding.

The self-expanding vascular implants used for the treatment of such aneurysms generally consist of a hollow-cylindrical metal framework of which the jacket surface is covered by a textile or polymer film, such that a hollow-cylindrical body is obtained. For implantation, the vascular prosthesis is radially compressed, such that its cross-sectional area is greatly reduced. With the aid of an insertion system, the vascular prosthesis is then brought into the region of the aneurysm, where it is released. By virtue of the resilience of the metal framework, the vascular prosthesis expands again to its original shape and in so doing stretches its jacket surface, which lodges inside the blood vessel proximally and distally in relation to the aneurysm. In this way, the blood now flows through the vascular prosthesis, and further loading of the bulge is avoided.

The metal framework of such vascular prostheses is generally composed of a wire mesh, for example, or of so-called stent springs, which are arranged in succession and extend circumferentially in a meandering formation and, if appropriate, are connected to each other by connecting struts made of wire, or which are merely connected to each other via the prosthesis material. The wire mesh or the stent springs are usually made of a shape-memory material, generally of Nitinol, as a result of which the stent springs, after introduction into a vessel for release, return to the expanded state and thus "wedge" the vascular implant.

Aneurysms generally occur in the region of the abdominal aorta or thoracic aorta. To treat aneurysms in the abdominal aorta or thoracic aorta, it is already known to stabilize the artery by implantation of a stent such that a rupture of the vessel is avoided.

However, aneurysms can also occur in what is called the ascending branch of the aorta (aorta ascendens). The ascending branch of the aorta is connected directly to the heart. Starting from the aortic root (sinus aortae), the ascending branch extends upward in a slightly curved shape away from the heart, merges there into the aortic arch (arcus aortae) and leads into the descending branch of the aorta (aorta descendens). The vessels of the head, among others the left and right carotid arteries, branch off in the area of the aortic arch. The aortic arch follows a curve of approximately 180° with a very narrow radius and connects the ascending branch of the aorta to the thoracic aorta and eventually to the abdominal aorta.

It is important, not only in the region of the aortic arch, to ensure that side vessels branching from the main vessel are not blocked by the positioning of the vascular prosthesis, which is why many vascular prostheses have open zones or so-called fenestrations through which branches issuing from the vascular implant, and protruding into the side vessels, can be inserted and can be fixed on the vascular implant.

Vascular diseases such as aneurysms or dissections in the region of the aortic arch have hitherto been generally treated by invasive open surgery. Such surgery has previously generally required two major interventions to be performed at different times and entails a very extensive, complex and therefore dangerous operation, since it is not just the heart but also the brain and the abdominal organs of the patient that have to be subjected to hypothermic perfusion, i.e. artificial, cold extracorporeal blood flow, or hypothermic arrest of blood flow. However, only a small number of heart surgeons at specialist centers are sufficiently familiar with such a procedure.

Moreover, stents and stent grafts or combinations of stents are also presently known that can be introduced in a minimally invasive procedure. In many patients with diseased vessels, however, these can only be used to a limited extent.

There is therefore still a great need for stents/stent graft systems, or vascular prostheses, that can be used for implantation in the region of the aortic arch and for treatment of vascular diseases in the region of the aortic arch.

SUMMARY

An object of the present invention is therefore to make available a vascular prosthesis and a vascular prosthesis system with which the region of the ascending aorta, the aortic arch and the descending aorta can be treated quickly and without complication in a large number of different patients with different vessel characteristics, and which also allows the above-described interventions to be performed by less experienced heart surgeons.

According to the present invention, this and other objects are solved by the provision of an intraluminal vascular prosthesis system for implantation in the region of the aortic arch of a patient, said system having at least the following: a hollow-cylindrical main vessel prosthesis, which has a lumen routed through the main vessel prosthesis, a first lumen end, a second lumen end, a hollow-cylindrical stent frame, optionally with a prosthesis material secured thereon, a length L1 and a diameter D1, wherein the hollow-cylindrical main vessel prosthesis is configured and dimensioned for implantation in the region of the aortic arch and the descending aorta of the patient, and wherein the main vessel prosthesis has at least one hollow-cylindrical anchoring vessel prosthesis, which has a lumen routed through the anchoring vessel prosthesis, a first lumen end, a second lumen end, a hollow-cylindrical stent frame, optionally with a prosthesis material secured thereon, a length L2 and a diameter D2, wherein the anchoring vessel prosthesis is securely attached within the lumen of the main vessel prosthesis, at least over part of the length L2 of the anchoring vessel prosthesis, and wherein the diameter D2 of the anchoring vessel prosthesis is at least 45% smaller than the diameter D1 of the main vessel prosthesis, and wherein the length L2 of the anchoring vessel prosthesis is shorter than the length L1 of the main vessel prosthesis.

According to another aspect of the invention, the intraluminal vascular prosthesis system according to the invention for implantation, in the region of the aortic arch, moreover has at least one hollow-cylindrical side vessel prosthesis, a lumen routed through the side vessel prosthesis that has a first lumen end, a second lumen end, a hollow-cylindrical stent frame, optionally with a prosthesis material secured thereon, a length L3 and a diameter D3, wherein the hollow-cylindrical side vessel prosthesis for implantation is designed and dimensioned to bridge the outlet of the subclavian artery or the carotid artery of the patient, in such a way that the side vessel prosthesis can be positioned with its first lumen end in the subclavian artery or the carotid artery, and, in order to securely anchor the side vessel prosthesis, its second lumen end can be inserted at least partially into and fixed in the lumen of the anchoring vessel prosthesis via the first lumen end of the anchoring vessel prosthesis.

The present invention also concerns a method for treating a vascular disease in the region of the aortic arch of a patient, and a method for the implantation of an intraluminal vascular prosthesis system into the aortic arch of a patient, said method comprising the following steps:

inserting and releasing the main vessel prosthesis in the region of the aortic arch and of the descending aorta, and inserting and releasing the side vessel prosthesis with its first lumen end in the subclavian artery or in the carotid artery and with its second lumen end at least partially in the lumen of the anchoring vessel prosthesis via the first lumen end of the latter.

This and other objects of the invention are fully achieved in this way.

With the novel vascular prosthesis or the novel vascular prosthesis system, it is possible for a weakened, damaged, torn or aneurysmal vessel, in particular in the region of the aortic arch, to be treated in a simple way. According to the invention, therefore, a vascular prosthesis is made available with which it is possible to simplify surgical interventions, in particular on the aortic arch, or in the ascending aorta, aortic arch and descending aorta, and to greatly reduce the time needed for these interventions.

In particular, by means of the vascular prosthesis according to the invention or the vascular prosthesis system according to the invention, it is possible to treat vessels which have side vessels branching off from them in the region of the site that is to be treated. By means of the particular design, the side vessels can continue to be supplied with blood via at least one side vessel prosthesis, wherein at the same time the damaged vessels are supported by the intraluminal vascular prosthesis. The insertion and placement of this system can be managed easily and with precision by virtue of its at least two-part design, composed of the hollow-cylindrical main vessel prosthesis together with the anchoring vessel prosthesis and the side vessel prosthesis.

In order to insert the vascular prosthesis system into a vessel of a patient to be treated, the intraluminal vascular prosthesis is first of all implanted at the desired location in the vessel, preferably in this case the aortic arch. A side vessel prosthesis is then implanted in the side vessel, wherein the first lumen end is positioned in the side vessel, while the second lumen end can be at least partially inserted into and fixed in the lumen of the anchoring vessel prosthesis, via the first lumen end of the latter, in order to securely anchor the side vessel prosthesis.

By virtue of the particular design, the vascular prosthesis and the side vessel prosthesis can be implanted separately from each other. The vascular prosthesis according to the invention and the vascular prosthesis system according to the invention therefore afford the advantage that it is not just highly specialized heart surgeons who can perform the above-described interventions on the aortic arch, but also inexperienced experts in the field. Moreover, the invention affords the advantage that the vascular prosthesis and the vascular prosthesis system can be adapted to the particular anatomical conditions of the patient who is to be treated.

By virtue of the design of the vascular prosthesis system according to the invention, in which the side vessel prosthesis is at least partially anchored or "plugged" in the anchoring vessel prosthesis, vessels that are very different anatomically can be treated using the same vascular prosthesis system. This can be achieved by the different plugging-in/anchoring depth of the side vessel prosthesis in the anchoring vessel prosthesis. If the side vessels are located farther away from the actual main vessel prosthesis, the chosen plugging-in depth can be smaller, in contrast to a greater anchoring depth in the case of side vessels that are located close by.

The implantation of the vascular prosthesis system is simplified in particular by the fact that the main vessel prosthesis does not have to be oriented precisely with respect to the side vessels that branch off. The orientation can be corrected by the "anchoring system" according to the invention and by the associated respective plugging-in/anchoring depth of the side vessel prosthesis in the anchoring vessel prosthesis. It is precisely the orientation of a one-part vascular prosthesis known from the prior art, with respect to side vessels that branch off, that makes not only the implantation of such implants difficult but also their production.

According to an aspect of the invention, the main vessel prosthesis, the at least one anchoring vessel prosthesis and the at least one side vessel prosthesis can be present as a covered or uncovered stent, i.e. optionally covered at least partially with a prosthesis material, or have a prosthesis material secured on the stent frame. Depending on the damage in the vessel and on the anatomical circumstances, it may be expedient that at least one of the vessel prosthesis parts listed has no prosthesis material, for example the side vessel prosthesis or the anchoring vessel prosthesis.

In particular, according to one aspect of the present invention, the main vessel prosthesis, if it does not have a prosthesis material, has a fenestration region, i.e. a region via which the side vessel prosthesis can be at least partially inserted and anchored in the lumen of the anchoring vessel prosthesis that is present in the lumen of the main vessel prosthesis. This fenestration region can be chosen, for example, from fenestration regions in the prosthesis material, individual openings in the jacket region of the main vessel prosthesis, or an open region, which extends about the entire circumference of the main vessel prosthesis in this region.

Alternatively, by way of the first lumen end of the main vessel prosthesis, the side vessel prosthesis can be at least partially inserted and anchored in the lumen of the anchoring vessel prosthesis that is present in the lumen of the main vessel prosthesis.

Moreover, according to another aspect of the invention, the main vessel prosthesis can have at least two stent frame portions or consist of at least two stent frame portions which are connectable to each other, for example by partial insertion of the second stent frame portion into the first stent frame portion.

According to another aspect of the vascular prosthesis according to the invention, said vascular prosthesis has a plurality of anchoring vessel prostheses. The number of anchoring vessel prostheses is tailored primarily to the number of side vessels which branch off and which are intended to be treated by the side vessel prostheses.

According to another aspect of the present invention, the first lumen end of the main vessel prosthesis and the first lumen end of the anchoring vessel prosthesis are arranged flush.

Here, "arranged flush" means that the anchoring vessel prosthesis is oriented with its first lumen end at the first lumen end of the main vessel prosthesis, and therefore both lumen ends terminate as it were on the same plane. In this embodiment, the anchoring vessel prosthesis thus extends from the first lumen end of the main vessel prosthesis through the lumen of the main vessel prosthesis in the direction of the second lumen end, along the inner wall of the main vessel prosthesis. Access to the anchoring vessel prosthesis by a side vessel prosthesis is thus not obtained through a side wall or a fenestration in the main vessel prosthesis but instead via the first lumen end of the main vessel prosthesis.

Although they will be clear to a person skilled in the art and from the present disclosure, some of the terms used here are defined in more detail below.

In the case of stent grafts or endoluminal prostheses, the respective ends are in principle generally designated, as here, by the terms "distal" and "proximal", where the term "distal" designates that part or end lying farther downstream in relation to the blood flow. By contrast, the term "proximal" designates, again in relation to the blood flow, a part or the end lying farther upstream in relation to the blood flow. To put it another way, the term "distal" means in the direction of the blood flow, and the term "proximal" means counter to the direction of the blood flow. In catheters, by contrast, or insertion systems, the term "distal" designates the end of the catheter or insertion system that is introduced into the patient, or the end farthest away from the user, and the term "proximal" designates the end directed closer toward the user.

Correspondingly, in the present case, the "proximal" opening and the "distal" opening of the vascular implant are the openings by which the flow of blood through the hollow-cylindrical lumen of the vascular implant is ensured: when the vascular implant according to the invention is implanted in a blood vessel, for example the aorta, the blood coming from the heart therefore flows through the proximal opening of the vascular implant and leaves the vascular implant through the distal openings thereof. The hollow-cylindrical main vessel prosthesis or its anchoring vessel prosthesis, and also the side vessel prosthesis, can in this case have a uniform diameter, or else different diameters, along the entire length thereof.

According to an aspect of the invention, the hollow-cylindrical stent frame is a metal frame generally consisting, for example, of a wire mesh or of so-called stent springs, which are arranged one behind the other, extend in a meandering formation and, if appropriate, are connected to one another by connecting struts made of wire, or which are merely connected to one another via the prosthesis material. The wire mesh or the stent springs are usually made of a shape-memory material, generally of Nitinol, as a result of which, after implantation into a vessel for release, the stent springs return to the expanded state and thus "open up" the vascular prosthesis.

According to one aspect of the vascular prosthesis system according to the invention, the main vessel prosthesis and/or the anchoring vessel prosthesis and/or the side vessel prosthesis have/has a stent frame and a prosthesis material secured on the latter.

In the present case, "stent frame" denotes any metal frame structure which, by an opening-up or an expansion of the frame, gives a vascular prosthesis an expansion force for keeping a vessel open, if appropriate in combination with a prosthesis material secured on the frame. The prosthesis material preferably consists of a biocompatible material, which means that contact between the vascular implant and the vessel wall does not cause complications.

In this connection, it is preferable if the prosthesis material has a material chosen from a textile or a polymer. It is in particular preferable if the prosthesis material has or is formed by a material chosen from polyester, polyurethane, polystyrene, polytetrafluoroethylene, ultra-high molecular weight polyethylene (UHMPE), or mixtures thereof.

According to another aspect of the vascular prosthesis system according to the invention, the stent frame of the main vessel prosthesis and/or the stent frame of the anchoring vessel prosthesis and/or the stent frame of the side vessel prosthesis is chosen from a laser-cut stent frame, individual stent springs or a braided stent frame.

A "stent frame" is understood here as any design of a stent in which different wire strands are intertwined, interlaced or otherwise coupled to form a structure with zones, regions or points at which the strands lie over one another, and with zones or regions that are free of the wire strands and that therefore form openings or windows or meshes. Accordingly, a laser-cut stent support frame also has meshes or openings. The openings, meshes or windows are preferably diamond-shaped here.

A "stent spring" is understood in the present case as being any one-piece annular element that can be compressed on the basis of its material and, after removal of the compressive pressure, can expand again in the manner of a spring.

According to an aspect of the invention, the stent frame of the main vessel prosthesis and/or the stent frame of the anchoring vessel prosthesis and/or the stent frame of the side vessel prosthesis has non-interconnected stent rings, which are arranged in succession and extend circumferentially in a meandering formation, and a prosthesis material firmly connected to the stent rings.

In the present case, a "stent ring" is understood as being any one-piece annular element which is formed by a wire extending in a circle and has a substantially round circumference. The wire of the stent ring can extend in an undulating formation, with alternating peaks and valleys that form a phase or amplitude. In the present case, "meandering formation" is understood to mean any loop-shaped course of the stent ring or stent wire.

The prosthesis material of the vascular prostheses that is to be used in the system according to the invention is optional or (in the case of the stent rings) obligatory and preferably has a material chosen from a textile or a polymer.

The prosthesis material of the main vessel prosthesis and/or of the anchoring vessel prosthesis and/or of the side vessel prosthesis, insofar as each of these or only one or two thereof have a prosthesis material, can be formed from such a material or have such a material.

According to another aspect of the invention, the meandering course of at least one stent ring of the stent frame has a non-uniform amplitude.

In this embodiment, a vascular prosthesis system is made available which can be used in particular in curved vessels, for example the aortic arch, since the non-uniform amplitudes mean that there is no unnecessary accumulation of material in the vascular prosthesis in the region of the curvature.

According to one aspect of the invention, the stent frame of the main vessel prosthesis and/or the stent frame of the anchoring vessel prosthesis and/or the stent frame of the side vessel prosthesis is self-expandable.

This means that the stent frame can be transferred from a compressed state to an expanded state, wherein the compressed state is achieved by an element, e.g. a sheath, which compresses the stent frame, and if appropriate the prosthesis material secured on the latter, and can be withdrawn, which sheath, for insertion into a vessel, is located over the stent frame and compresses it. After correct placement, the element compressing the stent frame is removed, whereupon the stent frame expands and its walls press onto the vessel wall, as a result of which the vascular prosthesis is fixed in the vessel.

It is generally preferable if the stent frame is made of a self-expandable material or has such a material. It is particularly preferable here if the material is Nitinol.

According to an aspect of the invention, the diameter D1 of the main vessel prosthesis is from 24 mm to 42 mm, in particular 24 mm, 26 mm, 28 mm, 30 mm, 32 mm, 34 mm, 36 mm, 38 mm, 40 mm or 42 mm.

According to an aspect of the invention, the diameter D2 of the anchoring vessel prosthesis is from 6 mm to 14 mm, in particular 6 mm, 7 mm, 8 mm, 9 mm, 10 mm, 11 mm, 12 mm, 13 mm or 14 mm.

According to another aspect of the invention, the diameter D3 of the side vessel prosthesis is from 6 mm to 16 mm, in particular 6 mm, 7 mm, 8 mm, 9 mm, 10 mm, 11 mm, 12 mm, 13 mm, 14 mm, 15 mm or 16 mm.

In these embodiments, the diameters D1, D2 and D3 can be adapted to the particular vessel that is to be treated. The stated measurements correspond in particular to the diameters within the aortic arch or the brachiocephalic trunk, the common carotid artery and the left subclavian artery. According to the invention, the main vessel prosthesis, the anchoring vessel prosthesis and the side vessel prosthesis can have a uniform diameter, or else different diameters, along the entire length thereof. If the respective vascular prosthesis parts have a different diameter, then the stated diameters D1, D2 and D3 of these embodiments correspond to the greatest or maximum diameters.

According to a further aspect of the invention, the anchoring vessel prosthesis in the lumen of the main vessel prosthesis is mounted on an inner wall, preferably by sewing, adhesive bonding or welding.

Secure fastening of the anchoring vessel prosthesis in the lumen of the main vessel prosthesis is preferred, since the anchoring vessel prosthesis may otherwise accidentally come loose from the main vessel prosthesis. This securing can be ensured by the embodiment. On account of its design, the anchoring vessel prosthesis is not itself anchored in the vessel, for example like the main vessel prosthesis or the side vessel prosthesis. On account of a strong blood flow inside the vascular prosthesis, the anchoring vessel prosthesis may therefore come loose and accidentally move. This disadvantage is avoided by the described embodiment.

According to a further aspect of the invention, the second lumen end of the side vessel prosthesis is insertable, via the first lumen end of the main vessel prosthesis, into the first lumen end of the anchoring vessel prosthesis and at least partially into the lumen thereof.

In this embodiment, it is easy for side vessels to be provided with a side vessel prosthesis. By means of the system for anchoring the side vessel prosthesis in the anchoring vessel prosthesis, it is also possible for an inexperienced heart surgeon to perform such implantations, since the main vessel prosthesis does not necessarily have to be oriented precisely with respect to the side vessels. An error occurring during implantation and concerning the location of the main vessel prosthesis can be remedied by the insertion of the prostheses into one another.

According to a further aspect of the invention, the main vessel prosthesis has a jacket surface, and a fenestration which is provided in the jacket surface and via which the second lumen end of the side vessel prosthesis is insertable into the lumen of the main vessel prosthesis and at least partially into the lumen of the anchoring vessel prosthesis via the first lumen end of the latter.

Fenestrated vascular prostheses are understood as those that have pre-formed holes (fenestrations) in order to permit one or more vessel outlets in the vascular prosthesis. According to this embodiment, it is possible for blood vessels branching off to the sides to be further supplied with blood via a side vessel prosthesis and, at the same time, for the main vessel to be supported by a main vessel prosthesis.

Alternatively, the fenestration can be configured as an in situ fenestration. In this case, the fenestration is introduced only after the vascular prosthesis has been positioned in the vessel. Here, the main vessel prosthesis is penetrated in situ with a needle in order to form a needle hole in the jacket surface of the prosthesis material. Thereafter, a dilator is pushed through the needle hole in order to widen the needle hole.

The jacket surface is preferably configured from a prosthesis material which is connected to the stent frame of the main vessel prosthesis.

According to a further aspect of the invention, the intraluminal vascular prosthesis system is used for the treatment of vascular diseases of a patient, in particular in the region of the aortic arch and of the descending aorta.

According to a further aspect of the invention of the method, the side vessel prosthesis is inserted into the lumen of the anchoring vessel prosthesis via the first lumen end of the main vessel prosthesis.

According to a further aspect of the invention, in the method presented herein, the main vessel prosthesis has a jacket surface and a fenestration provided in the jacket surface, and the side vessel prosthesis is inserted via the fenestration in the main vessel prosthesis into the lumen of the main vessel prosthesis and at least partially into the lumen of the anchoring vessel prosthesis via the first lumen end of the latter.

The features, properties and advantages that have been described for the vascular prosthesis according to the invention or the vascular prosthesis system according to the invention also apply correspondingly to the methods according to the invention.

Further advantages will become clear from the figures and from the following description of preferred illustrative embodiments.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

Illustrative embodiments of the invention are explained in more detail in the following description and shown in the drawing, in which.

EMBODIMENTS

In the figures, identical features are provided with identical reference signs. For the sake of clarity, the figures do not always show all of the reference signs.

Figure 1:
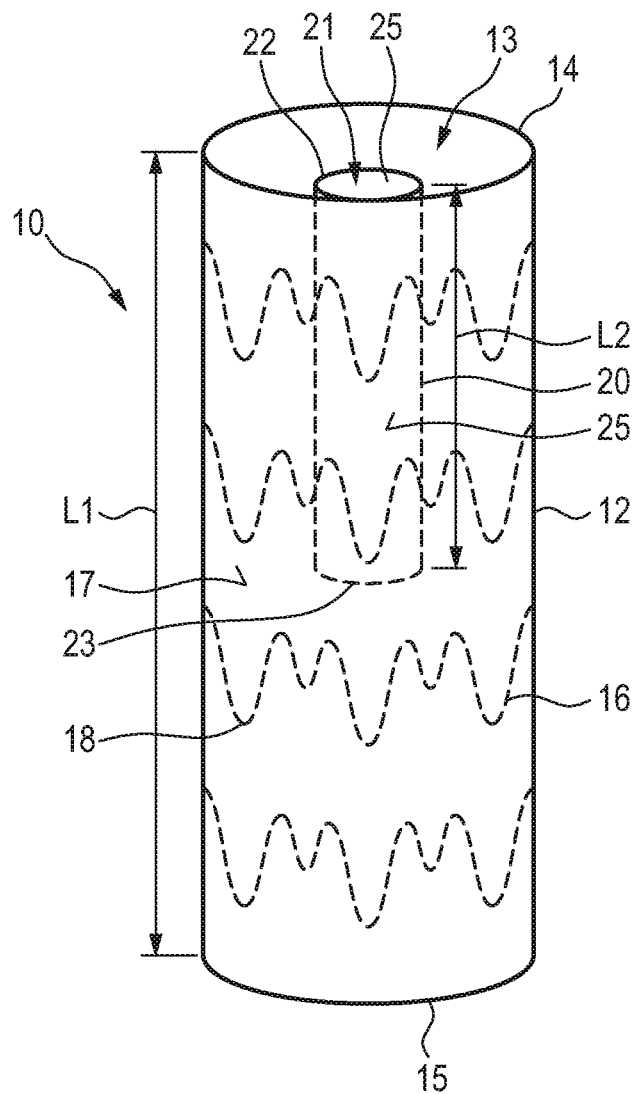
FIG. 1 shows a schematic view of a first embodiment of a main vessel prosthesis of an intraluminal vascular prosthesis according to the invention.
Figure 1:
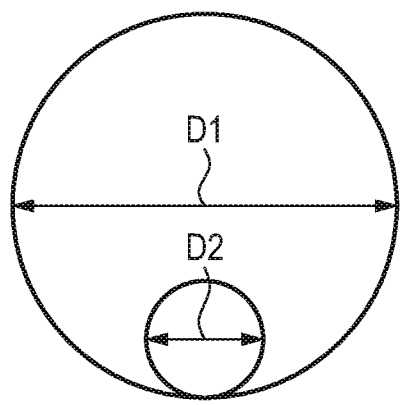

FIG. 1 shows a schematic view of parts of a first embodiment of an intraluminal vascular prosthesis system according to the invention. The vascular prosthesis system 10 shown here has two separate vessel prostheses, which are fixedly connected to each other: on the one hand, the main vessel prosthesis 12 and on the other hand the anchoring vessel prosthesis 20. The anchoring vessel prosthesis 20 can be secured to the main vessel prosthesis 12 by sewing, adhesive bonding or welding, for example. Both the main vessel prosthesis 12 and the anchoring vessel prosthesis 20 have a lumen 13 and 21, respectively. Said lumen extends in each case from the first lumen end 14 and 22 to the second lumen end 15 and 23, such that a length L1 and L2 is formed. The hollow-cylindrical structure of the main vessel prosthesis 12 and of the anchoring vessel prosthesis 20, with the diameters D1 and D2, is in particular obtained by the respective hollow-cylindrical stent frame 16 and 24 and by the respective surrounding prosthesis material 17 and 25. In this view, the stent frame 16 and 24 is in each case constructed from individual stent rings 18 and 26, which are only connected to one another via the prosthesis material 17 and 18.

The dimension of the hollow-cylindrical main vessel prosthesis 12 corresponds approximately to the dimension of the aortic arch and of the descending aorta. This permits simple implantation in the vessel. Depending on the nature of the vessel presented by individual patients, the dimensions of the intraluminal vascular prosthesis system can be adapted. In particular, the diameter D1 of the main vessel prosthesis 12 is adapted to the diameter of the descending aorta in such a way that, in the expanded state, it is pressed onto the vessel wall. It is in some cases preferable if the main vessel prosthesis 12 and/or the anchoring vessel prosthesis 20 have/has a different diameter D1, D2, respectively, over the length L1, L2, respectively.

The anchoring vessel prosthesis 20 is fixedly mounted, at least over part of the length L2, inside the lumen 13 of the main vessel prosthesis, wherein the diameter D2 of the anchoring vessel prosthesis 20 is at least 45% shorter than the diameter D1 of the main vessel prosthesis 12. Moreover, the length L2 of the anchoring vessel prosthesis 20 is shorter than the length L1 of the main vessel prosthesis 12.

This design of the vascular prosthesis system according to the invention means that a large number of patients with different vessel characteristics are able to be treated in the region of the ascending aorta, the aortic arch and the descending aorta.

The hollow-cylindrical anchoring vessel prosthesis 20 lying to the inside serves in particular the purpose that a further hollow-cylindrical side vessel prosthesis 30 (not shown in this figure) can be inserted at least partially into and fixed within the lumen 21.

Figure 2:
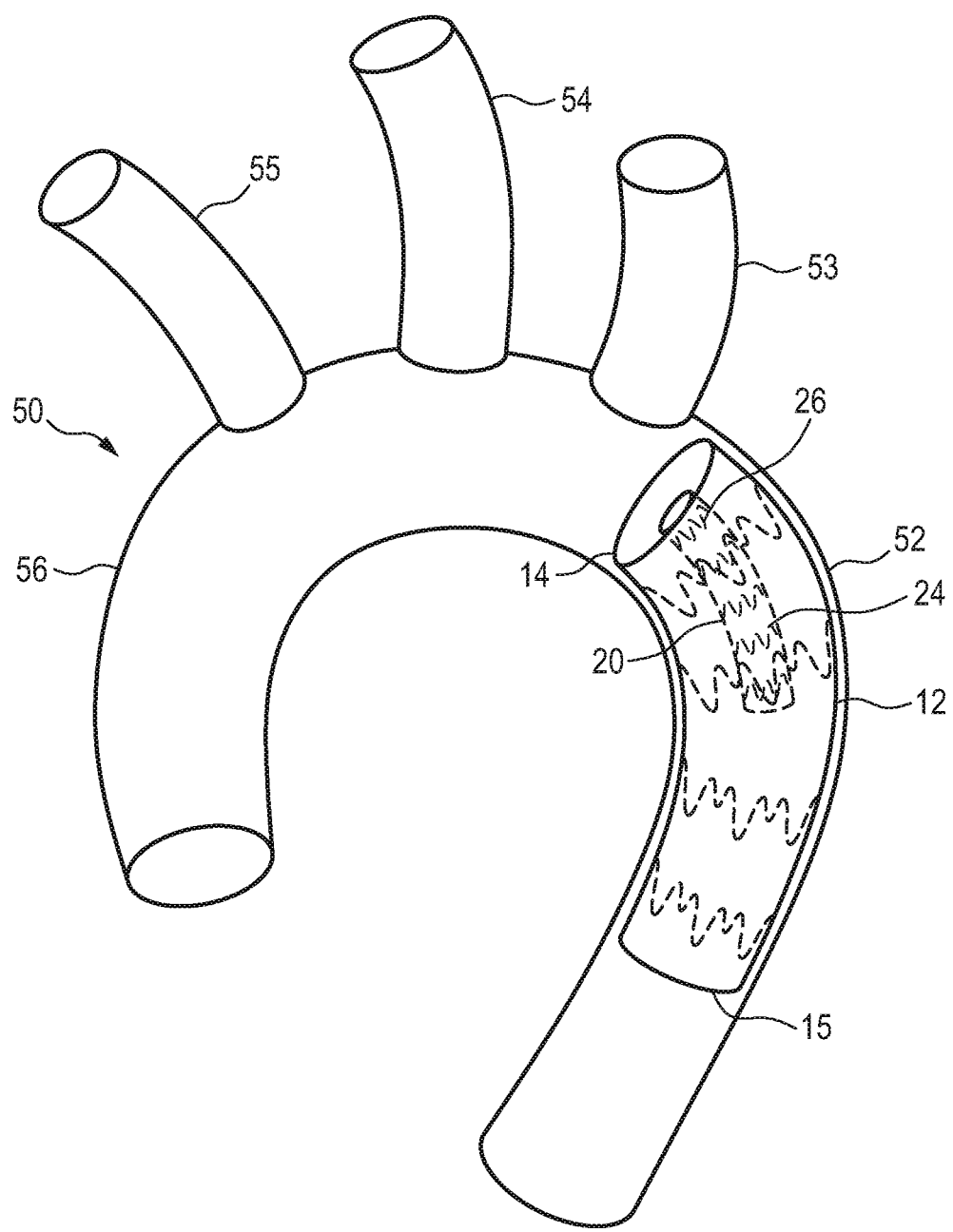
FIG. 2 shows a schematic view of the embodiment from FIG. 1, wherein the intraluminal main vessel prosthesis is present in the implanted state in the aortic arch or the descending aorta.

FIG. 2 shows a schematic view of the first embodiment of the intraluminal vascular prosthesis system according to the invention, wherein the intraluminal main vessel prosthesis 12 is present in the implanted state in the aortic arch 50 or in the region of the descending aorta 52.

The ascending branch of the aorta 56 is connected, via the aortic sinus (not shown in FIG. 2), to the left chamber of the heart (also not shown in FIG. 2). The ascending aorta 56 is connected to the descending aorta 52 via the aortic arch 50. Arterial vessels of the head have their origin in the region of the aortic arch 50, namely the brachiocephalic trunk 55, the common carotid artery 54 and the left subclavian artery 53.

In the view shown, the main vessel prosthesis 12 of the intraluminal vascular prosthesis system 10 bridges an aneurysm in the region of the descending aorta 52. The blood flow from the ascending aorta 56 passes through the aortic arch 50 into the first lumen end 14 of the main vessel prosthesis 12 and leaves the latter at the second lumen end 15. For this purpose, the main vessel prosthesis 12 has a hollow-cylindrical body on which a first lumen 13 forms. This lumen 13 is formed by meandering stent rings 18 which overall form the stent frame 16. The individual stent rings 18 are connected by a prosthesis material 17. The prosthesis material 17 is preferably a textile material or a film and is fixed to the stent rings 18 by sewing, gluing or melting in.

The anchoring vessel prosthesis 20 can be surrounded by a prosthesis material 25. If it has no prosthesis material 25, then the individual stent rings 26 are designed in such a way that they form a continuous stent frame 24.

The main vessel prosthesis 12 is preferably implanted in the vessel in such a way that a side vessel prosthesis 30 can be inserted into the lumen 21 in a manner taking up as little space as possible in the anchoring vessel prosthesis 20. This means that the side vessel prosthesis 30 is connected to the anchoring vessel prosthesis 20 in such a way that no accumulation of material takes place.

Figure 3A:
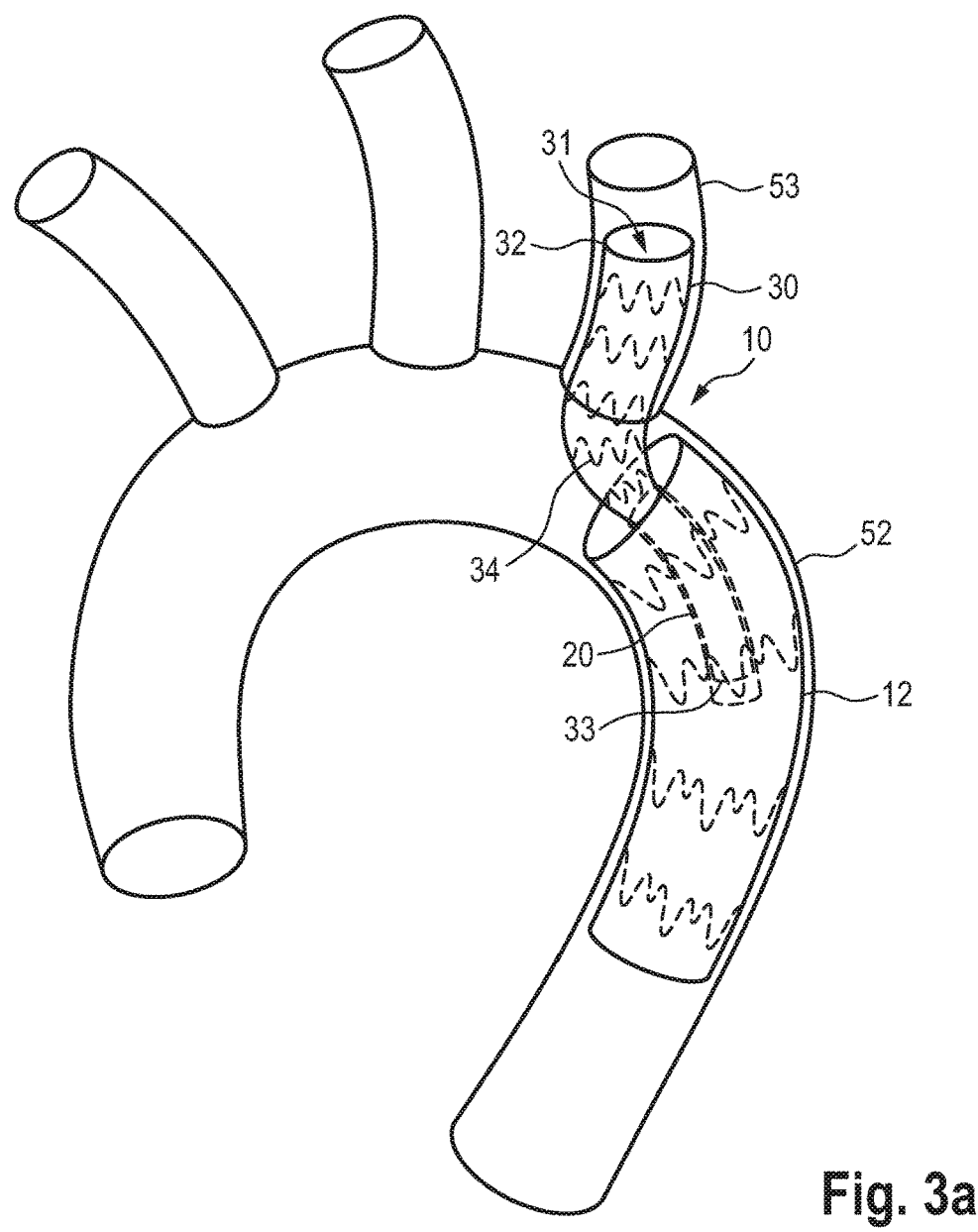
FIG. 3a shows a schematic view of a first embodiment of the intraluminal vascular prosthesis system according to the invention, wherein the intraluminal vascular prosthesis system is present in the implanted state in the aortic arch or the descending aorta.

FIG. 3a shows a schematic view of a first embodiment of the intraluminal vascular prosthesis system 10 according to the invention, wherein the intraluminal vascular prosthesis system 10 is present in the implanted state in the aortic arch 50 or the descending aorta 52. The intraluminal vascular prosthesis system 10 has a main vessel prosthesis 12 and a side vessel prosthesis 30. The main vessel prosthesis 12 corresponds here to the main vessel prosthesis 12 already described with reference to FIG. 2.

The side vessel prosthesis 30 with a length L3 has a continuous lumen 31, which extends from the first lumen end 32 to the second lumen end 33. The lumen 31 is formed in particular from the hollow-cylindrical stent frame 34, which is in turn formed from individual stent rings 36. In this view, the individual stent rings 36 are interconnected and not surrounded by a prosthesis material. In this configuration, the blood coming from the aortic arch can flow through the stent frame 34 into the branching-off side vessel 53. At the same time, the side vessel 53 is supported by the side vessel prosthesis 30.

In an embodiment not shown, the side vessel prosthesis 30 can also be surrounded only partially by a prosthesis material 35, preferably in the region of the second lumen end 33.

FIG. 3a shows a schematic view of a first embodiment of the hollow-cylindrical side vessel prosthesis 30. The side vessel prosthesis 30 has a lumen 31, which extends from the first lumen end 32 to the second lumen end 33. The length L3 of the side vessel prosthesis 30 is also defined thereby. In this view, the side vessel prosthesis 30 has stent rings 36 which are interconnected by a prosthesis material 35. The prosthesis material 35 and the individual stent rings 36 together form the hollow-cylindrical stent frame 36.

In this configuration, the side vessel prosthesis 30 tapers toward the second lumen end 33. The diameter D3 corresponds in this view to the greater diameter at the first lumen end 32. In this configuration, the diameter at the first lumen end 32 corresponds to the diameter of the side vessel into which the side vessel prosthesis 30 is intended to be implanted, and the diameter at the second lumen end 33 corresponds to the diameter of the anchoring vessel prosthesis 20 into which the side vessel prosthesis 30 is intended to be inserted.

Figure 4:
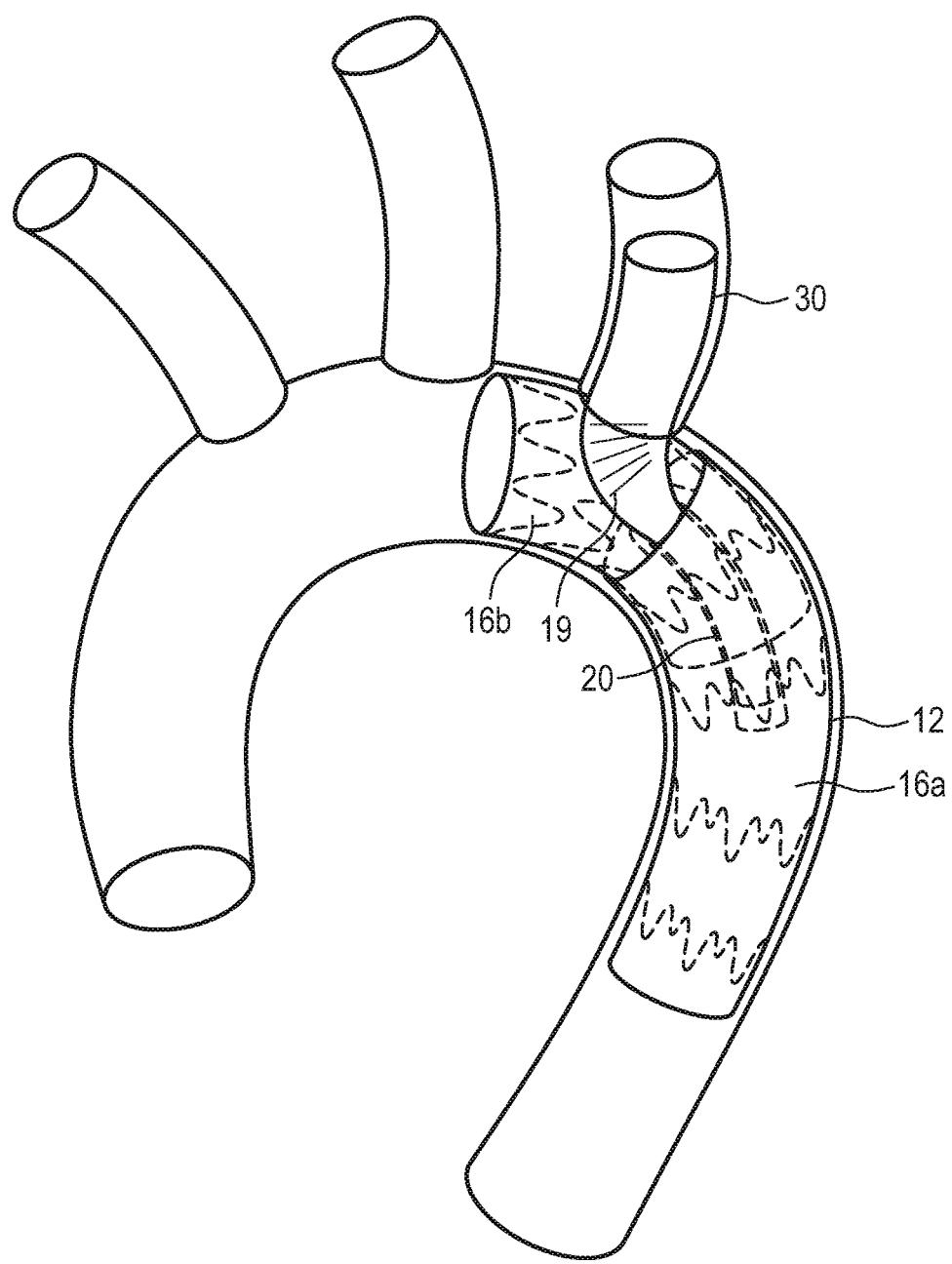
FIG. 4 shows a schematic view of a second embodiment of the intraluminal vascular prosthesis system according to the invention, wherein the intraluminal vascular prosthesis system is present in the implanted state in the aortic arch or the descending aorta.

FIG. 4 shows a schematic view of a second embodiment of the intraluminal vascular prosthesis system 10 according to the invention, wherein the intraluminal vascular prosthesis system 10 is present in the implanted state in the aortic arch 50 or the descending aorta 52.

Figure 3B:
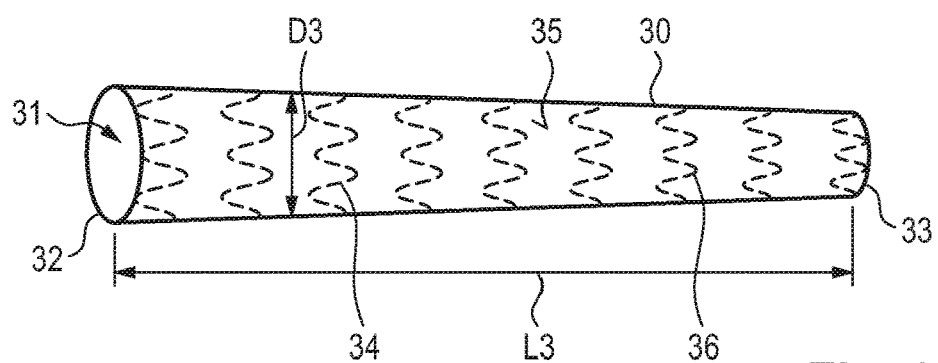
FIG. 3b shows a schematic view of a first embodiment of the hollow-cylindrical side vessel prosthesis.

The vascular prosthesis system 10 in FIG. 4 differs from the vascular prosthesis system 10 shown in FIG. 3 in the fenestration or fenestration region 19 present in the jacket surface. Through this fenestration 19, the second lumen end 33 of the side vessel prosthesis 30 is at least partially insertable into the lumen 13 of the main vessel prosthesis 12 and via the first lumen end 22 of the anchoring vessel prosthesis 20 into the lumen 13 of the latter. A fenestration 19 can be configured as pre-formed holes or as in situ fenestration. By means of the side vessel prosthesis 30, which is pushed through the fenestration 19, the side vessels can continue to be supplied with blood. This configuration affords the advantage that, in addition to the aortic arch 50 and descending aorta 52, the vascular prosthesis system 10 also supports the subclavian artery 53.

According to a further embodiment, provision can thus also be made, as shown in FIG. 4, that the main vessel prosthesis is composed of two interconnectable hollow-cylindrical stent frame portions 16a, 16b, such that a first stent frame portion 16a has the anchoring prosthesis 20, and the second stent frame portion 16b can be connected to the first stent frame portion 16a in order to lengthen the latter. The side vessel prosthesis 30 can then be inserted through the second stent frame portion 16b into the common lumen and into the anchoring prosthesis 20 present in the first stent frame portion 16a.

As a positioning aid during the implantation and as a means of checking the position of the individual components of the vascular prosthesis system 10, it is possible for X-ray markers (not shown) to be mounted at defined positions. For example, such X-ray markers are mounted in the region of the lumen ends 14, 15, 22, 23, 32 and/or 33 or in the region of the fenestration 19.

What is claimed is:

1. An intraluminal vascular prosthesis system configured for implantation in a region of an aortic arch of a patient, comprising:
a hollow-cylindrical main vessel prosthesis, which has a lumen routed through the main vessel prosthesis, a first lumen end, a second lumen end, a hollow-cylindrical stent frame, with a prosthesis material secured thereon, a length L1 and a diameter D1, wherein the hollow-cylindrical main vessel prosthesis is configured and dimensioned for implantation in the region of the aortic arch and a descending aorta of the patient, and wherein the main vessel prosthesis has at least one hollow-cylindrical anchoring vessel prosthesis, which has a lumen routed through the anchoring vessel prosthesis, a first lumen end, a second lumen end, a hollow-cylindrical stent frame, with a prosthesis material secured thereon, a length L2 and a diameter D2, wherein the anchoring vessel prosthesis is securely attached within the lumen of the main vessel prosthesis, at least over part of the length L2 of the anchoring vessel prosthesis, and wherein the diameter D2 of the anchoring vessel prosthesis is at least 45% smaller than the diameter D1 of the main vessel prosthesis, and wherein the length L2 of the anchoring vessel prosthesis is shorter than the length L1 of the main vessel prosthesis, wherein the first lumen end of the main vessel prosthesis and the first lumen end of the anchoring vessel prosthesis are flush with one another,
wherein the vascular prosthesis system further comprises:
at least one side vessel prosthesis, with a lumen routed through the side vessel prosthesis, wherein the side vessel prosthesis has a first lumen end, a second lumen end, a hollow-cylindrical stent frame, with a prosthesis material secured thereon, a length L3 and a diameter D3, and wherein the hollow-cylindrical side vessel prosthesis for implantation is designed and dimensioned to bridge the outlet of a subclavian artery and/or a carotid artery of the patient, in such a way that the side vessel prosthesis can be positioned with its first lumen end in the subclavian artery and/or the carotid artery, and, in order to securely anchor the side vessel prosthesis, its second lumen end can be inserted at least partially into and fixed in the lumen of the anchoring vessel prosthesis via the first lumen end of the anchoring vessel prosthesis.

2. The intraluminal vascular prosthesis system as claimed in claim 1, wherein one or more of the main vessel prosthesis, the anchoring vessel prosthesis, and the side vessel prosthesis have a stent frame and a prosthesis material secured on the stent frame.

3. The intraluminal vascular prosthesis system as claimed in claim 1, wherein the stent frame of the main vessel prosthesis and/or the stent frame of the anchoring vessel prosthesis and/or the stent frame of the side vessel prosthesis is chosen from a laser-cut stent frame, individual stent springs or a braided stent frame.

4. The intraluminal vascular prosthesis system as claimed in claim 1, wherein the stent frame of the main vessel prosthesis and/or the stent frame of the anchoring vessel prosthesis and/or the stent frame of the side vessel prosthesis has non-interconnected stent rings, which are arranged in succession and extend circumferentially in a meandering formation, and a prosthesis material fixedly connected to the stent rings.

5. The intraluminal vascular prosthesis system as claimed in claim 4, wherein the meandering circumferential course of at least one stent ring of at least one of the stent frames has a non-uniform amplitude.

6. The intraluminal vascular prosthesis system as claimed in claim 1, wherein the stent frame of the main vessel prosthesis and/or the stent frame of the anchoring vessel prosthesis and/or the stent frame of the side vessel prosthesis is self-expandable.

7. The intraluminal vascular prosthesis system as claimed in claim 1, wherein the diameter D1 of the main vessel prosthesis is between 24 mm and 42 mm.

8. The intraluminal vascular prosthesis system as claimed in claim 1, wherein the diameter D2 of the anchoring vessel prosthesis is between 6 mm and 14 mm.

9. The intraluminal vascular prosthesis system as claimed in claim 1, wherein the diameter D3 of the side vessel prosthesis is between 6 mm and 16 mm.

10. The intraluminal vascular prosthesis system as claimed in claim 1, wherein the anchoring vessel prosthesis, in the lumen of the main vessel prosthesis, is mounted on an inner wall, by sewing, adhesive bonding or welding.

11. The intraluminal vascular prosthesis system as claimed in claim 1, wherein the second lumen end of the side vessel prosthesis is insertable, via the first lumen end of the main vessel prosthesis, into the first lumen end of the anchoring vessel prosthesis and at least partially into the lumen thereof.

12. The intraluminal vascular prosthesis system as claimed in claim 1, wherein the main vessel prosthesis has a jacket surface, and a fenestration, which is provided in the jacket surface and via which the second lumen end of the side vessel prosthesis is insertable into the lumen of the main vessel prosthesis and at least partially into the lumen of the anchoring vessel prosthesis via the first lumen end of the anchoring vessel prosthesis.

13. The intraluminal vascular prosthesis system as claimed in claim 1, wherein the diameter of the side vessel prosthesis decreases from the first lumen end to the second lumen end.

14. The intraluminal vascular prosthesis system as claimed in claim 1, wherein the diameter of the side vessel prosthesis at the first lumen end is configured to match a diameter of a side vessel into which the side vessel prosthesis is to be inserted.

15. The intraluminal vascular prosthesis system as claimed in claim 1, wherein the diameter of the side vessel prosthesis decreases from the first lumen end to the second lumen end, and the diameter at the second end is substantially the same as a diameter of the anchoring vessel prosthesis.

16. A method for implantation of an intraluminal vascular prosthesis system into an aortic arch of a patient the intraluminal vascular prosthesis system including a hollow-cylindrical main vessel prosthesis, which has a lumen routed through the main vessel prosthesis, a first lumen end, a second lumen end, a hollow-cylindrical stent frame, with a prosthesis material secured thereon, a length L1 and a diameter D1, wherein the hollow-cylindrical main vessel prosthesis is configured and dimensioned for implantation in the region of the aortic arch and a descending aorta of the patient, and wherein the main vessel prosthesis has at least one hollow-cylindrical anchoring vessel prosthesis, which has a lumen routed through the anchoring vessel prosthesis, a first lumen end, a second lumen end, a hollow-cylindrical stent frame, with a prosthesis material secured thereon, a length L2 and a diameter D2, wherein the anchoring vessel prosthesis is securely attached within the lumen of the main vessel prosthesis, at least over part of the length L2 of the anchoring vessel prosthesis, and wherein the diameter D2 of the anchoring vessel prosthesis is at least 45% smaller than the diameter D1 of the main vessel prosthesis, and wherein the length L2 of the anchoring vessel prosthesis is shorter than the length L1 of the main vessel prosthesis, wherein the first lumen end of the main vessel prosthesis and the first lumen end of the anchoring vessel prosthesis are flush with one another, wherein the method comprises:
  inserting and releasing the main vessel prosthesis in a region of the aortic arch and of a descending aorta,
  inserting and releasing a side vessel prosthesis with its first lumen end in a subclavian artery and/or in a carotid artery and with its second lumen end at least partially in the lumen of the anchoring vessel prosthesis via the first lumen end of the anchoring vessel prosthesis.

17. The method as claimed in claim 16, wherein the side vessel prosthesis is inserted into the lumen of the anchoring vessel prosthesis via the first lumen end of the main vessel prosthesis.

18. The method as claimed in claim 16, wherein the main vessel prosthesis has a jacket surface and a fenestration provided in the jacket surface, and in that the side vessel prosthesis is inserted via the fenestration in the main vessel prosthesis into the lumen of the main vessel prosthesis and at least partially into the lumen of the anchoring vessel prosthesis via the first lumen end of the anchoring vessel prosthesis.

19. A method for treating a vascular disease in an aortic arch of a subject in need thereof, the method comprising:
  providing an intraluminal vascular prosthesis system including a hollow-cylindrical main vessel prosthesis, which has a lumen routed through the main vessel prosthesis, a first lumen end, a second lumen end, a hollow-cylindrical stent frame, with a prosthesis material secured thereon, a length L1 and a diameter D1, wherein the hollow-cylindrical main vessel prosthesis is configured and dimensioned for implantation in the region of the aortic arch and a descending aorta of the patient, and wherein the main vessel prosthesis has at least one hollow-cylindrical anchoring vessel prosthesis, which has a lumen routed through the anchoring vessel prosthesis, a first lumen end, a second lumen end, a hollow-cylindrical stent frame, with a prosthesis material secured thereon, a length L2 and a diameter D2, wherein the anchoring vessel prosthesis is securely attached within the lumen of the main vessel prosthesis, at least over part of the length L2 of the anchoring vessel prosthesis, and wherein the diameter D2 of the anchoring vessel prosthesis is at least 45% smaller than the diameter D1 of the main vessel prosthesis, and wherein the length L2 of the anchoring vessel prosthesis is shorter than the length L1 of the main vessel prosthesis, wherein the first lumen end of the main vessel prosthesis and the first lumen end of the anchoring vessel prosthesis are flush with one another,
  inserting and releasing the main vessel prosthesis of the intraluminal vascular prosthesis system in a region of the aortic arch and of the descending aorta, inserting and releasing a side vessel prosthesis with its first lumen end in a subclavian artery and/or in a carotid artery and with its second lumen end at least partially in the lumen of the anchoring vessel prosthesis via the first lumen end of the anchoring vessel prosthesis, thereby treating the vascular disease.

\* \* \* \* \*